United States Patent
Pradhan et al.

(10) Patent No.: US 9,394,292 B2
(45) Date of Patent: Jul. 19, 2016

(54) RIVAROXABAN INTERMEDIATE AND PREPARATION THEREOF

(71) Applicant: WANBURY LTD., Navi Mumbai, Maharashtra (IN)

(72) Inventors: Nitin Sharadchandra Pradhan, Maharastra (IN); Nilesh Sudhir Patil, Maharastra (IN); Rajesh Ramchandra Walavalkar, Maharastra (IN); Nilesh Subhas Kulkarni, Maharastra (IN); Sandip Babanrao Pawar, Maharastra (IN); Tarak Sambhaji Pawar, Maharastra (IN)

(73) Assignee: WANBURY LTD., Navi Mumbai, Maharashtra (IN)

( * ) Notice: Subject to any disclaimer, the term of this patent is extended or adjusted under 35 U.S.C. 154(b) by 0 days.

(21) Appl. No.: 14/436,035

(22) PCT Filed: Dec. 24, 2013

(86) PCT No.: PCT/IN2013/000799
§ 371 (c)(1),
(2) Date: Apr. 15, 2015

(87) PCT Pub. No.: WO2014/102820
PCT Pub. Date: Jul. 3, 2014

(65) Prior Publication Data
US 2015/0299175 A1    Oct. 22, 2015

(30) Foreign Application Priority Data
Dec. 26, 2012    (IN) .......................... 3358/MUM/2012

(51) Int. Cl.
*C07D 265/32*        (2006.01)
*C07D 413/10*        (2006.01)
*C07D 413/14*        (2006.01)

(52) U.S. Cl.
CPC ............ *C07D 413/10* (2013.01); *C07D 265/32* (2013.01); *C07D 413/14* (2013.01)

(58) Field of Classification Search
CPC .................................................... C07D 265/32
See application file for complete search history.

(56) References Cited

U.S. PATENT DOCUMENTS

| | | |
|---|---|---|
| 7,157,456 B2 | 1/2007 | Straub et al. |
| 7,351,823 B2 | 4/2008 | Berwe et al. |
| 7,585,860 B2 | 9/2009 | Straub et al. |
| 7,592,339 B2 | 9/2009 | Straub et al. |
| 7,932,278 B2 | 4/2011 | Thomas et al. |
| 8,101,601 B2 | 1/2012 | Lerchen et al. |

FOREIGN PATENT DOCUMENTS

| | | |
|---|---|---|
| WO | 0147919 A1 | 7/2001 |
| WO | 2004060887 A1 | 7/2004 |
| WO | 2007039132 A1 | 4/2007 |
| WO | 2009023233 A1 | 2/2009 |
| WO | 2010124385 A1 | 11/2010 |
| WO | 2011012321 A1 | 2/2011 |
| WO | 2011080341 A1 | 7/2011 |
| WO | 2011098501 A1 | 8/2011 |
| WO | 2012140061 A1 | 10/2012 |
| WO | 2012153155 A1 | 11/2012 |
| WO | 2012159992 A1 | 11/2012 |
| WO | 2014102822 A2 | 7/2014 |

OTHER PUBLICATIONS

United States Patent and Trademark Office (ISR/US), "International Search Report for PCT/IN2013/000799", US, Jan. 14, 2015.
PUBCHEM, Compound Summary for 446292-10-0, Create Date: Oct. 26, 2006, retrieved on Apr. 24, 2015, retrieved from the Internet, <URL: https://pubchem.ncbi.nlm.nih.gov/compound/11346837?from=summary>.
PUBCHEM, Compound Summary for CID 76684975, Create Date: Aug. 4, 2014, retrieved on Apr. 24, 2015, retrieved from the Internet, <URL: https://pubchem.ncbi.nlm.nih.gov/compound/176684975?from=summary>.
Jianyong Yuan et al., A Novel Synthesis of the Oxazolidinone Antithrombotic Agent Rivaroxaban, Molecules, 2014, p. 14999-15004, vol. No. 19, Issue No. 9.
Susanne Roehrig et al., Discovery of the Novel Antithrombotic Agent 5-Chloro- N -({(5 S )-2-oxo-3- [4-(3-oxomorpholin-4-yl)phenyl]-1,3-oxazolidin-5-yl}methyl)thiophene- 2-carboxamide (BAY 59/7939): An Oral, Direct Factor Xa Inhibitor, Journal of Medicinal Chemistry, 2005, pp. 5900-5908, vol. No. 48, Issue No. 19.

*Primary Examiner* — Michael Barker
*Assistant Examiner* — Karen Cheng
(74) *Attorney, Agent, or Firm* — Tim Tingkang Xia; Locke Lord LLP

(57) ABSTRACT

This invention relates to novel intermediate, formula (A) for rivaroxaban and process for the preparation thereof. Further it extends to the process for preparation of rivaroxaban by using the said novel intermediate, by treating with 5-chlorothiophene carbonyl chloride to form the rivaroxaban derivatives of formula (B). The obtained formula (B) further treated with acid to form rivaroxaban.

10 Claims, No Drawings

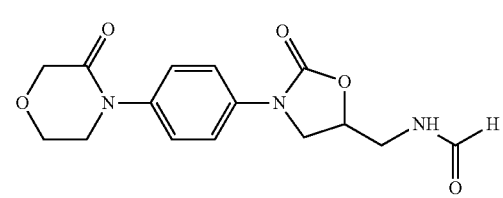

Formula (A)

RIVAROXABAN INTERMEDIATE AND PREPARATION THEREOF

FIELD OF INVENTION

The present invention relates to the field of synthesis of Rivaroxaban formula (I), and more particular to novel Rivaroxaban intermediate formula (A), and process for preparation thereof. Further the present invention relates to the process for preparation of Rivaroxaban by using novel intermediate formula (A).

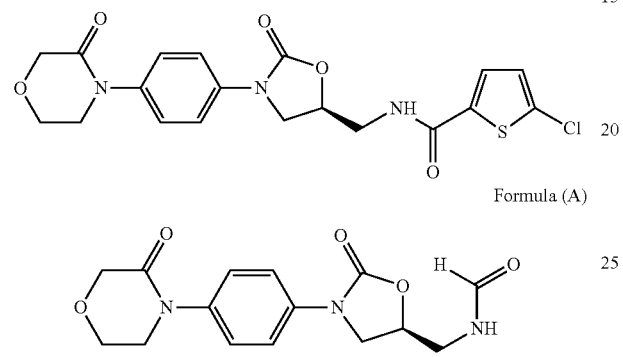

Formula (I)

Formula (A)

BACKGROUND OF INVENTION

Rivaroxaban, (5-chloro-N-{[(5S)-2-oxo-3[4-(3-oxomorpholin-4-yl)phenyl]oxazolidin-5-yl}methyl]thiophene-2-carboxamide) is a low molecular weight, orally administrable anticoagulant drug. The pharmaceutical directly inhibits the active form of serine protease Factor Xa (FXa). Rivaroxaban can be used for the prevention and treatment of various thromboembolic diseases, in particular of deep vein thrombosis (DVT), pulmonary embolism (PE), myocardial infarction, angina pectoris, reocclusions and restenoses after angioplasty or aortocoronary bypass, cerebral stroke, transitory ischemic attacks, and peripheral arterial occlusive diseases.
Rivaroxaban firstly disclosed in WO01/47919, by Bayer AG, and has following structure:

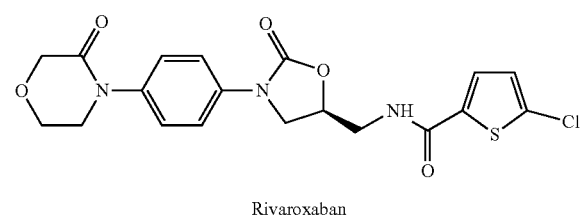 [SMILES: O=C(NC[C@H]1CN(c2ccc(N3CCOCC3=O)cc2)C(=O)O1)c1ccc(Cl)s1]

Rivaroxaban

US 2007/0149522, relates to a method for producing 5-chloro-N-{(5S)-2-oxo-3-[4-(3-oxo-4-morpholinyl)phenyl]-1,3-oxazolidin-5-yl}-methyl)thiophene-2-carboxamide starting from 5-chlorothiophene-2-carbonylchloride and (2S)-3-amino-propane-1,2-diol to obtain compound formula (VIII), which further treated with 4 equivalent hydrobromic acid in presence of acetic anhydride to get N-((S)-3-bromo-2-hydroxypropyl)-5-chlorothiophene-2-carboxamide; compound formula (IX). Further (4-aminophenyl)-3-morpholinone (III), treated with compound formula (IX), to obtain N-{(R)-2-hydroxy-3-[4-(3-oxomorpholin-4-yl)phenylamino]propyl}-5-chlorothiophene-2-carboxamide; compound formula (X), finally compound formula (X), may treated with phosgene or phosgene equivalent to give for example, phosgene replacements such as di- or triphosgene, or carbon monoxide equivalents, N,N-carbonylbisimidazole, N,N-carbonylbisimidazole in a solvent mixture of 1-methyl-2-pyrrolidone and toluene to obtain 5-chloro-N-({(5S)-2-oxo-3-[4-(3-oxo-4-morpholinyl)phenyl]-1,3-oxazolidin-5-yl}methyl)-2-thiophene-carboxamide (I).

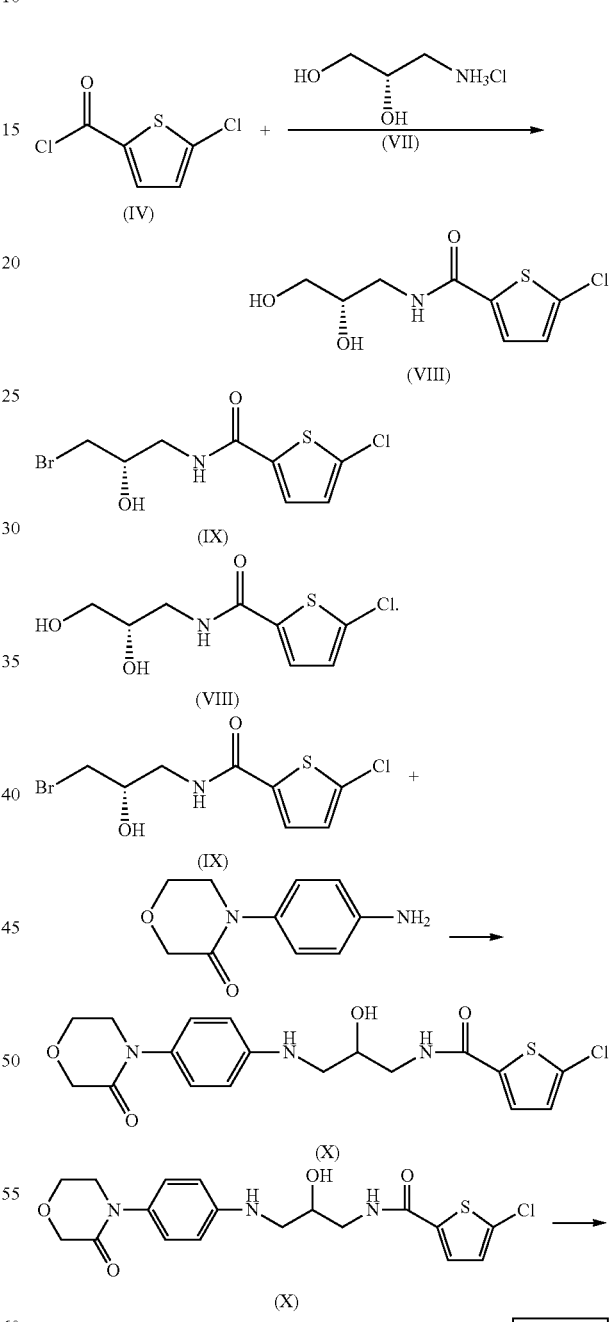

US2007/0066611, relates to a process for preparing 4-(4-aminophenyl)-3-morpholinone by reacting 4-(4-nitrophenyl)-3-morpholinone with hydrogen in the presence of a hydrogenation catalyst, characterized in that the reaction is effected in an aliphatic alcohol.

U.S. Pat. No. 7,598,378, relates to a process for preparing 4-(4-aminophenyl)-3-morpholinone by reacting 4-(4-nitrophenyl)-3-morpholinone with hydrogen in the presence of a hydrogenation catalyst, characterized in that the reaction is effected in an aliphatic alcohol.

U.S. Pat. No. 7,351,823, relates to a process for preparing 5-chloro-N-({(5S)-2-oxo-3-[4-(3-oxo-4-morpholinyl)phenyl]-1,3-oxazolidin-5-yl}methyl)-2-thiophenecarboxamide starting from 2-[(2S)-2-oxiranylmethyl]-1H-isoindole-1,3-(2H)-dione, 4-(4-aminophenyl)-3-morpholinone and 5-chlorothiophene-2-carbonyl chloride.

WO 2009/023233, relates to novel compounds that are substituted oxazolidinones derivatives and pharmaceutically acceptable salts thereof. More specifically, this invention relates to novel oxazolidinone compounds that are derivatives of Rivaroxaban. The invention also provides pyrogen-free compositions comprising one or more compounds of the invention and a carrier, along with the use of the disclosed compounds and compositions in methods of treating diseases and conditions that are beneficially treated by administering a selective inhibitor of factor Xa, such as Rivaroxaban.

By carefully inspection of above said patents and patent applications there is need to overcome the said drawbacks in process so in this connection the instant invention concern about the novel intermediate with process for preparation which is concomitantly used for the preparation of Rivaroxaban.

SUMMARY

The main aspect of the present invention is to provide novel intermediate of formula (A), for Rivaroxaban, and process for preparation thereof.

Another aspect of the present invention is to provide the novel process for the preparation of the Rivaroxaban formula (I) by using novel intermediate of formula (A).

Yet another aspect of the present invention is to provide the process for the preparation of the novel intermediate formula (A) by using intermediate formula (VII) in form of free base or acid addition salt.

Yet another aspect of the present invention is to provide novel intermediate of formula (A) in crystalline or amorphous form.

Yet another aspect, the process for preparation of Rivaroxaban formula (I) can be carried out in single pot by using novel compound formula (A) as a starting material.

Yet another aspect of the present invention is to provide a process for preparation of Rivaroxaban of formula (I), wherein the obtained Rivaroxaban is substantially free from impurities and thereby eliminating the required purification steps and further exert the efficient process for large scale preparation.

DETAILED DESCRIPTION OF THE INVENTION

Before the present invention is described, it is to be understood that this invention is not limited to particular methodologies and materials described, as these may vary as per the person skilled in the art. It is also to be understood that the terminology used in the description is for the purpose of describing the particular embodiments only, and is not intended to limit the scope of the present invention.

Before the present invention is described, it is to be understood that unless defined otherwise, all technical and scientific terms used herein have the same meaning as commonly understood by one of ordinary skill in the art to which this invention belongs. Further, it is to be understood that the present invention is not limited to the methodologies and materials similar or equivalent to those described herein can be used in the practice or testing of the present invention, the preferred methods and materials are described, as these may vary within the specification indicated. Unless stated to the contrary, any use of the words such as "including," "containing," "comprising," "having" and the like, means "including without limitation" and shall not be construed to limit any general statement that it follows to the specific or similar items or matters immediately following it. Embodiments of the invention are not mutually exclusive, but may be implemented in various combinations. The described embodiments of the invention and the disclosed examples are given for the purpose of illustration rather than limitation of the invention as set forth the appended claims. Further the terms disclosed embodiments are merely exemplary methods of the invention, which may be embodied in various forms.

A term herein "reflux temperature" means the temperature at which the solvent or, the solvent system refluxes or boils at atmospheric pressure.

The term "substantially free of" in reference to a composition, as used herein, means that an absent substance cannot be detected in the composition by methods known to those skilled in the art at the time of the filing of this application.

In one of the embodiments, the present invention provides an improved process for the preparation of Rivaroxaban of formula (I) comprises:

(a) reacting, 4-(4-aminophenyl)morpholine-3-one of formula (II) with 2-[(2S)-oxiran-2-ylmethyl]-1H-isoindole-1,3 (2H)-dione of formula (III) in a suitable solvent to obtain 2-[(2R)-2-hydroxy-3-{[4-(3-oxomorpholin-4-yl)phenyl]amino}propyl]-1H-isoindole-1,3(2H)-dione of formula (IV);

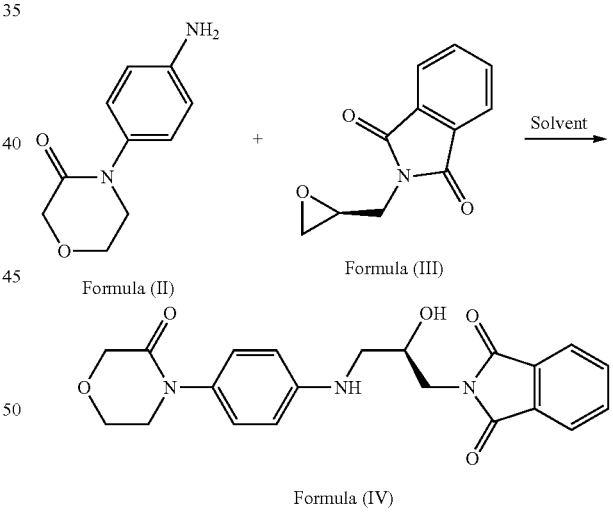

(b) preparing compound of formula (VI) by reacting compound of formula (IV) using di-1H-imidazol-1-ylmethanone of formula (V);

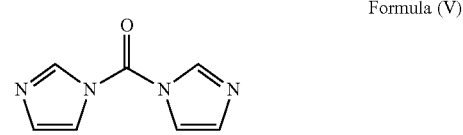 [SMILES: O=C(n1ccnc1)n1ccnc1]

Formula (V)

in suitable solvent and optionally in presence of a base;

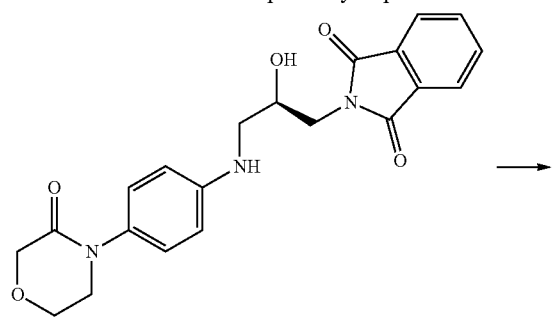

Formula (IV)

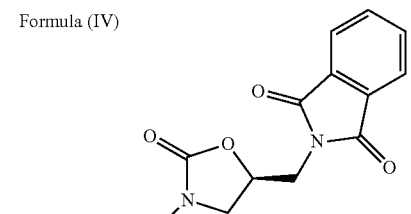

Formula (VI)

(c) eliminating the pthalamide group from compound of formula (VI), in suitable solvent using a suitable de-protecting agent in order to get free base of compound formula (VII), and further treated with acid to get acid addition salt of 4-{4-[(5S)-5-(aminomethyl oxo-1,3-oxazolidin-3-yl] phenyl}morpholin-3-one formula (VII);

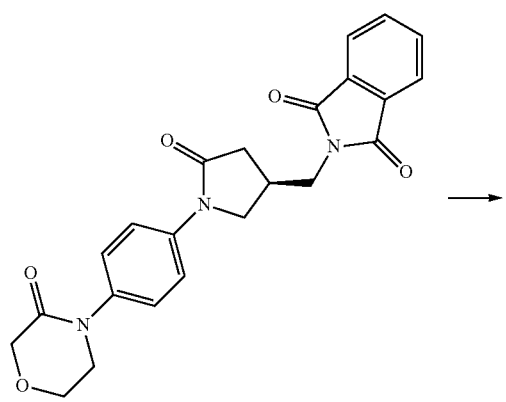

Formula (VI)

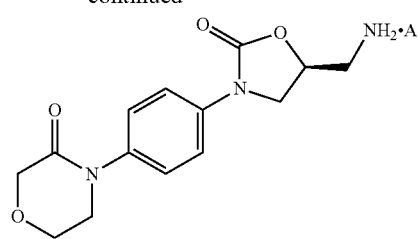

Formula - VII

A is acid addition salt; acid may be inorganic or organic acid;

(d) reacting compound of formula (VII) or free base of formula (VII) with inorganic or organic acid in suitable solvent, optionally in the presence of a base to obtain novel intermediate formula (A), N-({(5S)-2-oxo-3-[4-(3-oxomorpholin-4-yl)phenyl]-1,3-oxazolidin-5-yl}methyl)formamide;

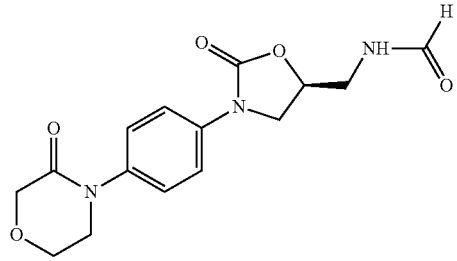

Formula - VII

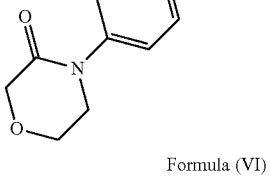

Formula (A)

(e) reacting novel compound formula (A) with compound formula (VIII) or 5-chlorothiophene-2-carbonitrile in suitable solvent and base in order to obtain the novel intermediate or precursor of Rivaroxaban formula (B), optionally in the presence of catalyst and/or activating agents;

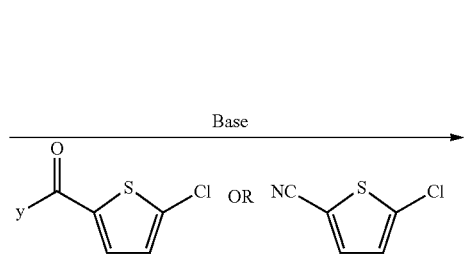

Formula (A)

Formula (VIII)

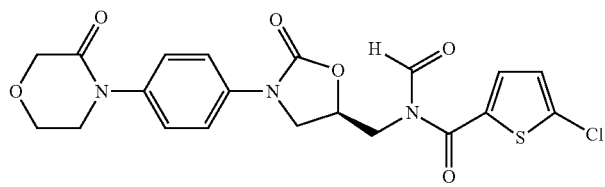

Formula (B)

Optionally Rivaroxaban of compound of formula (I), can be directly prepared without isolation of compound of formula (B);

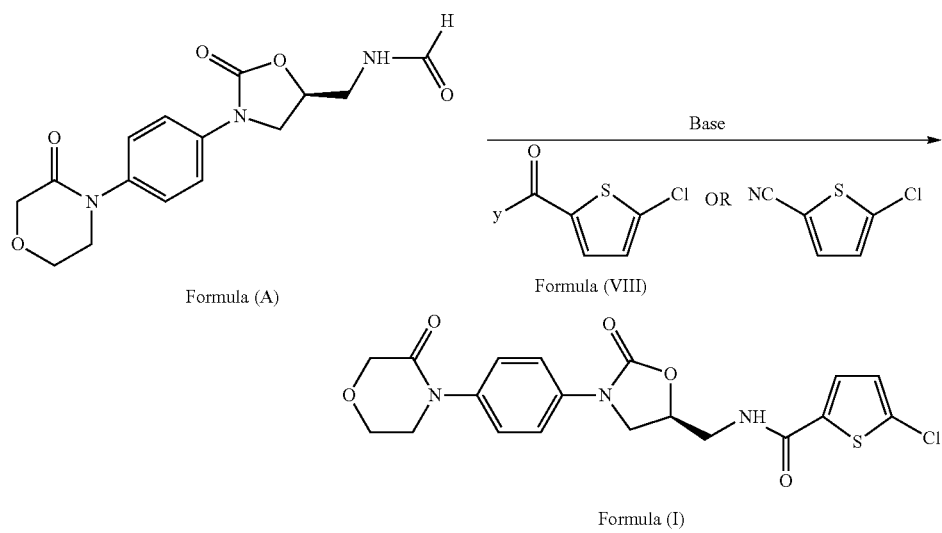

Wherein;

Y is sulfonyloxy, imidazole, triazole, tetrazole, alkoxy, substituted alkoxy, tri-halomethoxy, N-hydroxysuccinamide, hydroxy, esters, primary amine, secondary amine p-nitrophenol, N-hydroxythalamide, N-hydroxybenzotriazole, chlorine, fluorine, bromine & iodine. Base used may be inorganic or organic.

(f) treating compound formula (B) with acid or base in suitable solvent in order to depart the aldehyde group from compound formula (B) to obtain the title compound Rivaroxaban formula (I);

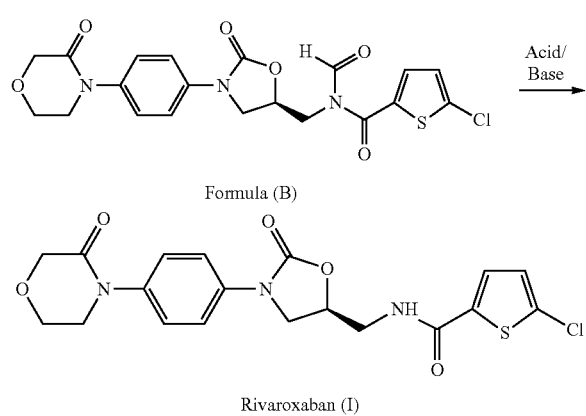

The instant invention further extend to the preparation of acid addition salt of compound formula (VII), in order to get the purified compound formula (A) without any further purification by acid-base treatment, or solvent crystallization.

The solvent used in step (a) and step (c) may be same or different; wherein the said solvent is an organic solvent selected from the group comprising aliphatic hydrocarbons, aromatic hydrocarbons, dialkylformamides, ethers, cyclic ethers, substituted cyclic ethers, alcohol, ketones, dialkylsulfoxides, dialkylacetamides, nitriles, ionic liquids, halogenated aliphatic hydrocarbons and water or mixtures thereof but more preferable solvent which is neutral towards the reactants.

The step (a) is carried out at temperature in the range of 0° C. to 95° C. Usually the reaction may be carried out at temperature up to reflux temperature of the said solvent.

The solvent used in step (b) for the preparation of compound of formula (VI) is an organic solvent selected from the group comprising of aliphatic hydrocarbons, aromatic hydrocarbons, dialkylformamides, ethers, cyclic ethers, substituted cyclic ethers, ketones, dialkylsulfoxides, dialkylacetamides, nitriles, ionic liquids, halogenated aliphatic hydrocarbons or mixtures thereof.

The solvent used in step (c) is an organic solvent selected from the group comprising aliphatic hydrocarbons, aromatic hydrocarbons, dialkylformamides, ethers, cyclic ethers, substituted cyclic ethers, dialkylsulfoxides, dialkylacetamides, nitriles, ionic liquids, halogenated aliphatic hydrocarbons and water or mixtures thereof. Further the compound formula (VII) may be prepared in terms of acid addition salt by using inorganic or organic acid.

In step (d), the compound of formula (VII), may be used in free base form or its acid addition salt. The solvent used in the step (d) is an organic solvent, may be mixture or water and organic solvent. Formylating agent used in the step (d) may be formic acid, alkyl formate etc. The solvent used in the reaction may be selected for the aromatic hydrocarbons, nitriles, aliphatic hydrocarbons, ethers, preferably aromatic hydrocarbon more preferably toluene and xylene. The base used in step (d), is selected from organic or inorganic base.

In step (e), compound formula (A), may be treated with formula (VIII), optionally in the presence of base which may be inorganic or organic in solvent selected from the group comprising aliphatic hydrocarbons, aromatic hydrocarbons, dialkylformamides, ethers, cyclic ethers, substituted cyclic ethers, dialkylsulfoxides, dialkylacetamides, nitriles, ionic liquids, esters, halogenated aliphatic hydrocarbons, ketones, cyclic amides and water or mixtures thereof to obtain Rivaroxaban precursor of formula (B). Activating agents used in the reaction of step (e) comprises CDI, DCC, HOBt, DMAP, EDCI, boric acid, boronic acid, phenyl boronic acid etc. and mixture thereof.

In step (f) compound formula (B) treated with acid or base in the presence of absence of the solvent. Solvent, acid, and base used in the reaction may be inorganic or organic. Suitable solvent selected for the step (f) from the group comprising aliphatic hydrocarbons, aromatic hydrocarbons, dialkylformamides, ethers, cyclic ethers, substituted cyclic ethers, esters, alcohols dialkylsulfoxides, dialkylacetamides, nitriles, ionic liquids, carboxylic acid, halogenated aliphatic hydrocarbons, ketones and water or mixtures thereof or optionally step (f) carried out in biphasic medium and optionally in presence of phase transfer catalyst.

According to another embodiment, the present invention provides the process for preparation of compound formula (A) comprises:

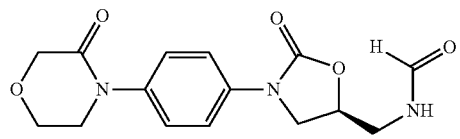

Formula (A)

treating formula (VII) in form of free base or acid addition salt with formylating agent

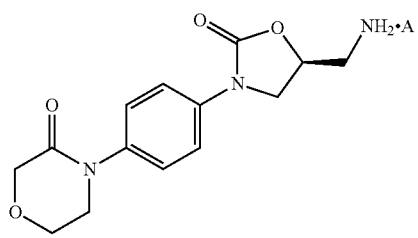

Formula - VII

Wherein;
A is acid addition salt and acid used may be inorganic or organic acid

The solvent used may be mixture or water and organic solvent. Formylating agent used may be formic acid, alkyl formate etc. The solvent used in the reaction may be selected for the aromatic hydrocarbons, nitriles, aliphatic hydrocarbons, ethers preferably aromatic hydrocarbon more preferably toluene and xylene. The base used is selected from organic or inorganic base.

According to another embodiment, the present invention provides the process for preparation of compound formula (B) comprises:

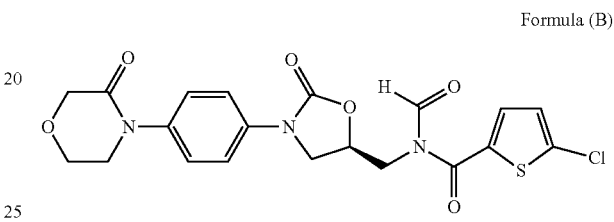

Formula (B)

treating novel intermediate formula (A);

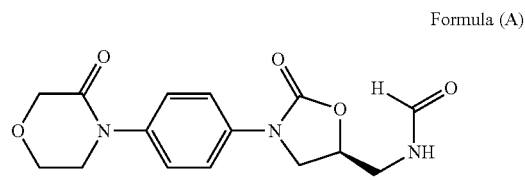 [SMILES: O=CNC[C@H]1CN(c2ccc(N3CCOCC3=O)cc2)C(=O)O1]

Formula (A)

with compound formula (VIII) OR (IX);

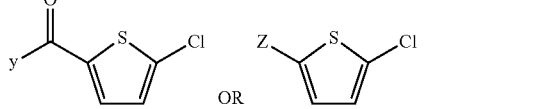

Formula (VIII)

Wherein;
Y is sulfonyloxy, imidazole, triazole, tetrazole, alkoxy, substituted alkoxy, tri-halomethoxy, N-hydroxysuccinamide, hydroxy, esters, primary amine, secondary amine p-nitrophenol, N-hydroxythalamide, N-hydroxybenzotriazole, chlorine, fluorine, bromine & iodine. Base used may be inorganic or organic.

Z is electron withdrawing substituent.

According to yet another embodiment Rivaroxaban of compound of formula (I), can be directly prepared from compound of formula (A), without isolation of compound of formula (B);

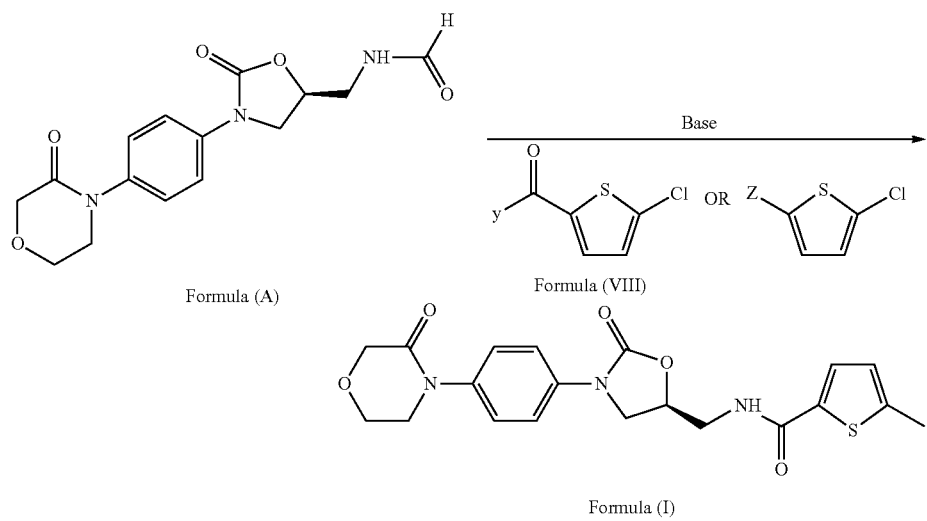

Wherein;

Y is sulfonyloxy, imidazole, triazole, tetrazole, alkoxy, substituted alkoxy, tri-halomethoxy, N-hydroxysuccinamide, hydroxy, esters, primary amine, secondary amine p-nitrophenol, N-hydroxythalamide, N-hydroxybenzotriazole, chlorine, fluorine, bromine & iodine. Base used may be inorganic or organic.

Z is electron withdrawing substituent.

The solvents used from the group comprising aliphatic hydrocarbons, aromatic hydrocarbons, dialkylformamides, ethers, cyclic ethers, substituted cyclic ethers, dialkylsulfoxides, dialkylacetamides, nitriles, ionic liquids, esters, halogenated aliphatic hydrocarbons, ketones, cyclic amides and water or mixtures thereof to obtain Rivaroxaban precursor of formula (B). Activating agents used in the reaction of step (e) comprises CDI, DCC, HOBt, DMAP, EDCI, boric acid, boronic acid, phenyl boronic acid etc. and mixture thereof. Optionally reaction may carried out in biphasic medium and preferably in the presence of phase transfer catalyst.

According to yet another embodiment, the present invention provides the process for preparation of compound formula (I) comprises:

Formula (I)

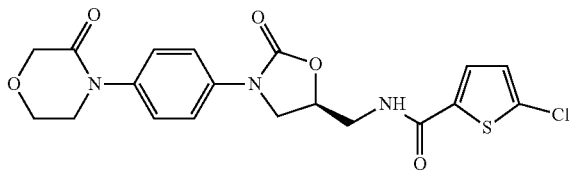

treating compound formula (B);

Formula (B)

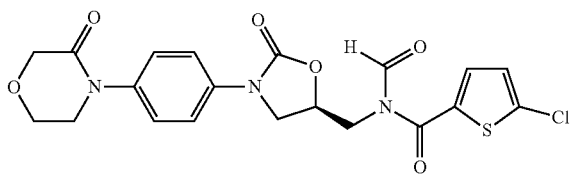

with acid or base is selected from inorganic or organic to obtain compound formula (I), and the solvent used for said reaction is an organic solvent selected from the group comprising aliphatic hydrocarbons, aromatic hydrocarbons, dialkylformamides, ethers, cyclic ethers, substituted cyclic ethers, esters, alcohols dialkylsulfoxides, dialkylacetamides, nitriles, ionic liquids, carboxylic acid, halogenated aliphatic hydrocarbons and water or mixtures thereof and optionally reaction may carried out in biphasic medium and optionally in presence of phase transfer catalyst.

The present invention is described in the examples given below; further these are provided only to illustrate the invention and therefore should not be construed to limit the scope of the invention.

EXAMPLE-1

Preparation of 2-((2R)-2-Hydroxy-3-{[4-(3-oxo-4-morpholinyl)phenyl]amino}propyl)-1H-isoindole-1,3(2H)-dione (Stage-I)

In a four neck round bottom flask charged Isopropyl alcohol (135 ml), 4-(4-aminophenyl) morpholin-3-one (10 g), 2-[(2s)-oxiran-2yl methyl]-1H-isoindole-1,3(2H)dione ((11.6 g) and water (15 ml) at 25 to 30° C. Slowly heated the reaction mixture to reflux and maintained for 24 h at reflux temperature. Reaction mass is cooled to 25 to 30° C. after completion of the reaction. Reaction mass then maintained at 25 to 30° C. for 30 minutes. Finally obtained solid is filtered off and washed by isopropyl alcohol (25 ml)

Yield 87.5%

EXAMPLE-2

Preparation of 2-([[(5S)-2-Oxo-3-[4-(3-oxo-4-morpholinyl)phenyl]-1,3-oxazolidin-5-yl}methyl)-1H-isoindole-1,3(2H)-dione (Stage-II)

In a four neck round bottom flask, charged dichloromethane (150 ml), 2-((2R)-2-Hydroxy-3-{[4-(3-oxo-4-morpholinyl)phenyl]amino}propyl)-1H-isoindole-1,3(2H)-dione (15 g), N,N'-dicarbonyldiimidazole (9.22 g), and powdered potassium carbonate (5.24 g) at 25 to 30° C. The obtained reaction mass then stirred for 5 h at 25 to 30° C. Reaction mass then filtered and obtained solid is washed the by dichloromethane. Separated filtrate is concentrated under reduced pressure to obtain residue. Added tetrahydrofuran (30 ml) to residue. The obtained mixture is heated to 40 to 45° C. for 30 minutes followed by cooling to room temperature. Finally obtained solid is filtered off and washed by tetrahydrofuran. Yield 90%

EXAMPLE-3

Preparation of 4-{4-[(5S)-5-(aminomethyl)-2-oxo-1,3-oxazolidin-3-yl]phenyl}morpholin-3-one hydrochloride (Stage-III)

In a four neck round bottom flask, charged methanol (100 ml), 2-([[(5S)-2-Oxo-3-[4-(3-oxo-4-morpholinyl)phenyl]-1,3-oxazolidin-5-yl}methyl)-1H-isoindole-1,3(2H)-dione (10 g), and 40% aqueous methylamine (5 g) at 25 to 30° C. Reaction mass is stirred for 1 h at 25 to 30° C. Added second lot of 40% aqueous methylamine (5 g) to reaction mass at 25 to 30° C. After complete addition of methylamine solution, reaction mass is heated to 60 to 65° C., and maintained at same temperature for 4 h. Reaction mixture then cooled to 25 to 30° C. and added conc. hydrochloric acid (2 ml, pH should be 1 to 2). Finally reaction mass is cooled to 10° C. and stirred for 30 minutes. Obtained solid is filtered off and washed by chilled methanol (10 ml). Yield 80%

EXAMPLE-4

Preparation of N-({(5S)-2-oxo-3-[4-(3-oxomorpholin-4-yl)phenyl]-1,3-oxazolidin-5-yl}methyl)formamide (aldehyde of primaryamine; Stage-IV)

In a four neck round bottom flask charged 4-{4-[(5S)-5-(aminomethyl)-2-oxo-1,3-oxazolidin-3-yl]phenyl}morpholin-3-one free base (50 g) toluene (350 ml) and formic acid (21.63 g). Reaction mass then heated azeotropically to 110-120° C. employing dean-stark apparatus for 3 to 4 h. (water removed azeotropically) Reaction mass is cooled to 25 to 30° C. Obtained solid is filtered off and washed by toluene.
Yield 96%

EXAMPLE-5

Preparation of N-({(5S)-2-oxo-3-[4-(3-oxomorpholin-4-yl)phenyl]-1,3-oxazolidin-5-yl}methyl)formamide (aldehyde of primaryamine; Stage-IV)

In a four neck round bottom flask charged 4-{4-[(5S)-5-(aminomethyl)-2-oxo-1,3-oxazolidin-3-yl]phenyl}morpholin-3-one free base (50 g) methylene dichloride OR ethylene dichloride (350 ml) and formic acid (21.63 g). Reaction mass then heated azeotropically to 110-120° C. employing dean-stark apparatus for 3 to 4 h. (water removed azeotropically) Reaction mass is cooled to 25 to 30° C. Obtained solid is filtered off and washed by toluene.
Yield 90%

EXAMPLE-6

Preparation of N-({(5S)-2-oxo-3-[4-(3-oxomorpholin-4-yl)phenyl]-1,3-oxazolidin-5-yl}methyl)formamide (aldehyde of primaryamine; Stage-IV)

In a four neck round bottom flask charged 4-{4-[(5S)-5-(aminomethyl)-2-oxo-1,3-oxazolidin-3-yl]phenyl}morpholin-3-one free base (50 g) ether (450 ml) and formic acid (21.63 g). Reaction mass then heated azeotropically to 110-120° C. employing dean-stark apparatus for 3 to 4 h. (water removed azeotropically) Reaction mass is cooled to 25 to 30° C. Obtained solid is filtered off and washed by toluene.
Yield 85%

EXAMPLE-7

Preparation of 5-chloro-N-formyl-N-({(5S)-2-oxo-3-[4-(3-oxomorpholin-4-yl)phenyl]-1,3-oxazolidin-5-yl}methyl)thiophene-2-carboxamide (Stage-V)

Added N-({(5 S)-2-oxo-3-[4-(3-oxomorpholin-4-yl)phenyl]-1,3-oxazolidin-5-yl}methyl)formamide (1 g), dichloromethane (25 ml) in a clean dry 4 neck R.B. flask at 25 to 30° C. To this clear solution added potassium carbonate (0.89 g) and stirred at 25 to 30° C. for 30 minutes. To this reaction mass, slowly added solution of 5-chlorothiophene-2-carbonyl chloride (1.0 g), and dichloromethane (5 ml). The obtained reaction mass then stirred at 25 to 30° C. for 5 to 6 h. Added water (25 ml) to reaction mass and separated organic layer. Obtained organic layer then washed by water (25 ml×2). Finally organic layer is dried over sodium sulfate and concentrated under reduced pressure to obtain residue. Added methanol (5 ml) to residue and heated to reflux to get clear solution. The obtained clear solution gradually cooled to 15 to 20° C. The precipitated solid then filtered off and washed by chilled methanol (1 ml).
Yield 0.3 g

EXAMPLE-8

Preparation of Rivaroxaban (Stage-VI)

5-chloro-N-formyl-N-({(5 S)-2-oxo-3-[4-(3-oxomorpholin-4-yl)phenyl]-1,3-oxazolidin-5-yl}methyl)thiophene-2-carboxamide (1.0 g) taken in mixture of acetic acid (5 ml) and conc hydrochloric acid (0.25 ml). Obtained reaction mixture is heated to 70 to 80° C. for 3 to 4 h. After completion of reaction, cooled reaction mixture 25 to 30° C. and added methanol (5 ml). The precipitated solid is filtered off and washed by methanol (3 ml).
Yield 0.6 g

EXAMPLE-9

Preparation of 5-chloro-N-({(5S)-2-oxo-3-[4-(3-oxomorpholin-4-yl)phenyl]-1,3-oxazolidin-5-yl}methyl)thiophene-2-carboxamide (Nitrite route)

To a solution of 4-{4-[(5S)-5-(aminomethyl)-2-oxo-1,3-oxazolidin-3-yl]phenyl}morpholin-3-one hydrochloride (5.7 g) in ethanol (70 ml) added potassium carbonate (7.1 g) and the mixture was stirred 2 h at 25 to 30° C. then filtered to obtain 4-{4-[(5S)-5-(aminomethyl)-2-oxo-1,3-oxazolidin-3-yl]phenyl}morpholin-3-one (free base). In another flask charged solution of 5-chlorothiophene-2-carbonitrile (2.9 g) under nitrogen in ethanolic HCl (12 ml) and stirred for 5 h at room temperature till white precipitate was obtained. Distilled under nitrogen to avoid from moisture and obtained residue added in solution of 4-{4-[(5S)-5-(aminomethyl)-2-oxo-1,3-oxazolidin-3-yl]phenyl}morpholin-3-one. The mixture was stirred for 16 to 18 h at reflux temperature. Added aq.ethanol (5 ml) and again heat the mixture at reflux temperature for 10 to 12 h to obtain 5-chloro-N-({(5S)-2-oxo-3-[4-(3-oxomorpholin-4-yl)phenyl]-1,3-oxazolidin-5-yl}methyl)thiophene-2-carboxamide (crud material) which further purified by column Chromatography.

EXAMPLE-10

Preparation of Rivaroxaban

N-({(5 S)-2-oxo-3-[4-(3-oxomorpholin-4-yl)phenyl]-1,3-oxazolidin-5-yl}methyl)formamide (1 g) taken in a dichloromethane(10 ml) and stirred reaction mass at 25 to 30° C. for 30 minutes. To this mixture added solution of 4-nitrophenyl-5-chlorothiophene-2-carboxylate (1.06 g) in a dichloromethane (10 ml) and sodium hydroxide (0.38 g) in water (5 ml) simultaneously through addition funnel. Obtained reaction mass then stirred for 1 to 2 h at 25 to 30° C. After completion of reaction, Separated organic layer and concentrated under reduced pressure to obtain residue. Added acetic acid and methanol to residue stirred for 30 minutes and obtained solid is filtered off. Washed solid with methanol.
yield 0.67 g

EXAMPLE-11

Preparation of Rivaroxaban

N-({(5S)-2-oxo-3-[4-(3-oxomorpholin-4-yl)phenyl]-1,3-oxazolidin-5-yl}methyl)formamide (1 g) taken in a mixture of tetrahydrofuran (10 ml) and sodium hydride (0.11 g) stirred reaction mass at 25 to 30° C. for 30 minutes. To this mixture added 5-chlorothiophene carbonyl chloride (0.86 g). Obtained reaction mass then stirred for 1 to 2 h at 25 to 30° C. After completion of reaction, added ethyl acetate and water. Separated organic layer and concentrated under reduced pressure to obtain residue. Added acetic acid and methanol to residue stirred for 30 minutes and obtained solid is filtered off. Washed solid with methanol
Yield 0.6 g,

EXAMPLE-12

Preparation of 2-([(5S)-2-Oxo-3-[4-(3-oxo-4-morpholinyl)phenyl]-1,3-oxazolidin-5-yl}methyl)-1H-isoindole-1,3(2H)-dione (Stage-II)

In a four neck round bottom flask, charged dichloromethane (3400 ml), 2-((2R)-2-Hydroxy-3-{[4-(3-oxo-4-morpholinyl)phenyl]amino}propyl)-1H-isoindole-1,3(2H)-dione (340 g) and N,N'-dicarbonyldiimidazole (209.13 g) at 25 to 30° C. The obtained reaction mass then stirred for 8 hr. at 25 to 30° C. Reaction mass is concentrated under reduced pressure to obtain residue. Added tetrahydrofuran (1700 ml) to residue. The obtained mixture is heated to 40 to 45° C. for 30 minutes followed by cooling to room temperature. Finally obtained solid is filtered off and washed by tetrahydrofuran (170 ml)
Yield=93.55%

EXAMPLE-13

Preparation of 4-{4-[(5S)-5-(aminomethyl)-2-oxo-1,3-oxazolidin-3-yl]phenyl}morpholin-3-one hydrochloride (Stage-III)

In a four neck round bottom flask, charged methanol (2900 ml), 2-([(5S)-2-Oxo-3-[4-(3-oxo-4-morpholinyl)phenyl]-1,3-oxazolidin-5-yl}methyl)-1H-isoindole-1,3(2H)-dione (290 g), and 40% aqueous methylamine (265 g) at 25 to 30° C. Reaction mass is stirred for 1 h at 25 to 30° C. and then heated to 60 to 65° C., and maintained at same temperature for 4 h. Reaction mixture then cooled to 25 to 30° C. and added conc. hydrochloric acid (290 ml, pH should be 1 to 2) and stirred for 30 minutes. Obtained solid is filtered off and washed by chilled methanol (290 ml).
Yield=92.0%

EXAMPLE-14

Preparation of N-({(5S)-2-oxo-3-[4-(3-oxomorpholin-4-yl)phenyl]-1,3-oxazolidin-5-yl}methyl)formamide (Stage-IV)

In a four neck round bottom flask charged 4-{4-[(5S)-5-(aminomethyl)-2-oxo-1,3-oxazolidin-3-yl]phenyl}morpholin-3-one Hydrochloride (250 g), Dichloromethane (1250 ml) and ammonia (250 ml) stir for 15 min and separate the layers, Take organic layer and add toluene (1250 ml), water(500 ml) and formic acid (140.6 g). Reaction mass then heated azeotropically to 110-120° C. employing dean-stark apparatus for 3 to 4 h. (water removed azeotropically) Reaction mass is cooled to 25 to 30° C. Obtained solid is filtered off and washed by toluene.
Yield=80.0%

EXAMPLE-15

Preparation of 5-chloro-N-formyl-N-({(5S)-2-oxo-3-[4-(3-oxomorpholin-4-yl)phenyl]-1,3-oxazolidin-5-yl}methyl)thiophene-2-carboxamide (Stage-V)

Added N-({(5S)-2-oxo-3-[4-(3-oxomorpholin-4-yl)phenyl]-1,3-oxazolidin-5-yl}methyl)formamide (120 g), dichloromethane (2400 ml) in a clean dry 4 neck R.B. flask at 25 to 30° C. cool the reaction mass to 0 to 5° C. To this solution added dropwise Diisopropylethyl amine (145.7 g) and solution of 5-chlorothiophene-2-carbonyl chloride (170 g), and dichloromethane (240 ml) at 0 to 5° C. The obtained reaction mass then stirred at 25 to 30° C. and heat to reflux for 12 hr. cool the reaction mass to 25 to 30° C. washed reaction mass with 10% citric acid solution (2×360 ml) and separated organic layer. Obtained organic layer then washed by water (600 ml×2), and concentrated under reduced pressure to obtain residue. Added methanol (600 ml) to residue and stir for 20 min. The precipitated solid then filtered off and washed by methanol (240 ml). suck dry and take the wet cake into flask add methanol (600 ml) and stir the solution for 30 min. solid then filtered off and washed by methanol (240 ml).
Yield=85.0%

EXAMPLE-16

Preparation of Rivaroxaban (Stage-VI)

In four neck round bottom flask charge 5-chloro-N-formyl-N-({(5S)-2-oxo-3-[4-(3-oxomorpholin-4-yl)phenyl]-1,3-oxazolidin-5-yl}methyl)thiophene-2-carboxamide (120 g), dichloromethane(2400 ml) and 70% methanesulphonic acid (120 ml) at 25-30° C. Obtained reaction mixture is heated to reflux for 4 to 5 h. After completion of reaction, concentrate reaction mass under reduced pressure to obtain residue. Added Dichloromethane (120 ml) and slowly added Methanol (600 ml) to the residue. The precipitated solid is filtered off and washed by methanol (240 ml)

Yield=80%

Preparation of Rivaroxaban (Stage-VI)

In four neck round bottom flask charge 5-chloro-N-formyl-N-({(5S)-2-oxo-3-[4-(3-oxomorpholin-4-yl)phenyl]-1,3-oxazolidin-5-yl}methyl)thiophene-2-carboxamide (120 g), dichloromethane (2400 ml) and hydrochloric acid OR sulphuric acid (120 ml) at 25-30° C. Obtained reaction mixture is heated to reflux for 4 to 5 h. After completion of reaction, concentrate reaction mass under reduced pressure to obtain residue. Added Dichloromethane (120 ml) and slowly added Methanol (600 ml) to the residue. The precipitated solid is filtered off and washed by methanol (240 ml)

Yield=75%

The invention claimed:

1. A compound of formula (A)

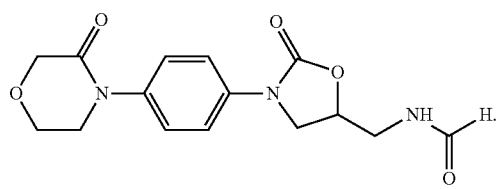

Formula (A)

2. A process for preparation of rivaroxaban by using compound formula (A), as claimed in claim 1 comprising:
   (a) treating 4-(4-aminophenyl)morpholine-3-one of formula (II) with 2-[(2S)-oxiran-2-ylmethyl]-1H-isoindole-1,3(2H)-dione of formula (III), in a suitable solvent to obtain 2-[(2R)-2-hydroxy-3-{[4-(3-oxomorpholin-4-yl)phenyl]amino}propyl]-1H-isoindole-1,3(2H)-dione of formula (IV);

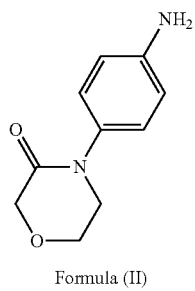 + 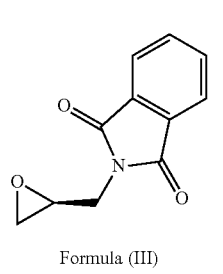 →Solvent→

Formula (II)        Formula (III)

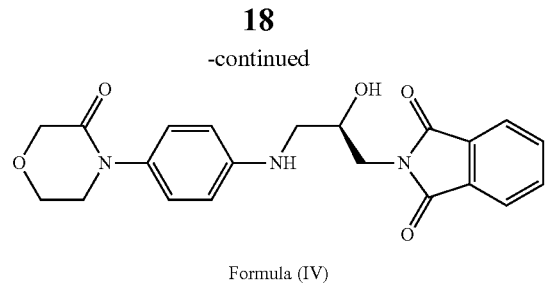

Formula (IV)

(b) reacting the compound of formula (IV) with di-1H-imidazol-1-ylmethanone of formula (V);

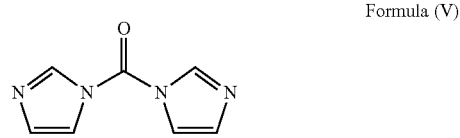 [SMILES: O=C(n1ccnc1)n1ccnc1]

Formula (V)

in a suitable solvent in presence of a base to obtain compound of formula (VI);

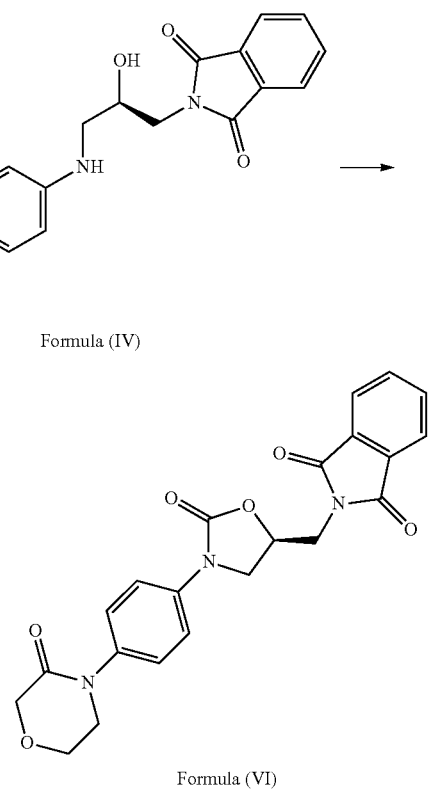

Formula (IV)

Formula (VI)

(c) deprotecting the compound of formula (VI) in a suitable solvent using a suitable de-protecting agent to get a compound of formula (VII), as a free base; optionally, treating compound of formula (VII) with an acid to provide an acid addition salt of compound of formula (VII);

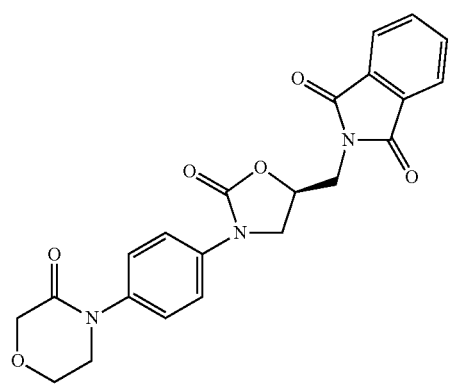

Formula VI

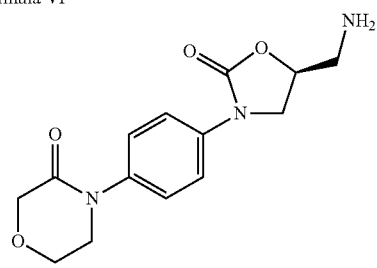

Formula VII (d) converting compound of formula (VII) or its acid addition salt obtained in step c) to a novel intermediate of formula (A), N-({(5S)-2-oxo-3-[4-(3-oxomorpholin-4-yl)phenyl]-1,3-oxazolidin-5-yl}methyl)formamide;

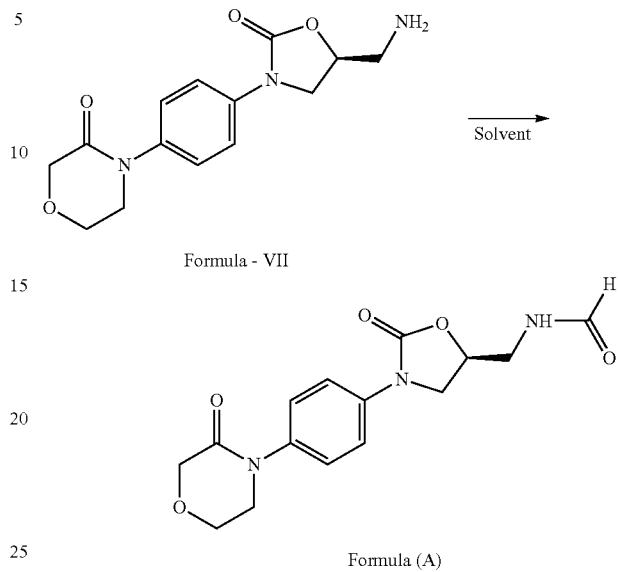

(e) treating compound formula (A) with compound formula (VIII) or 5-chlorothiophene-2-carbonitrile in suitable solvent (s) selected from methylene dichloride, acetone, toluene and ether or mixture thereof in presence of a base to obtain the compound formula (B);

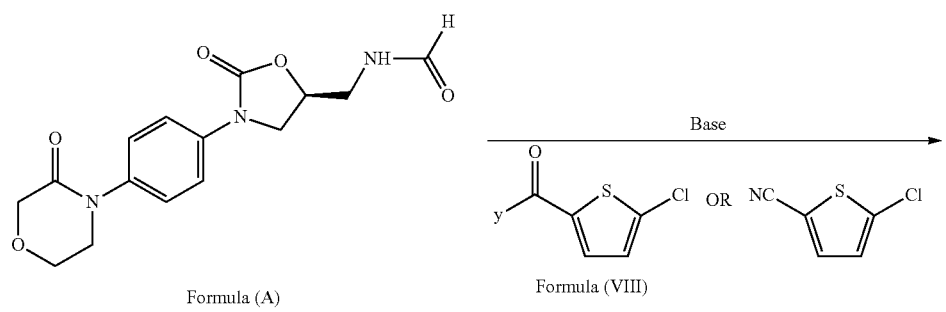

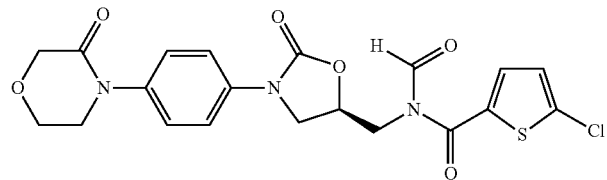

Formula (B)

wherein Y is sulfonyloxy, imidazole, triazole, tetrazole, alkoxy, substituted alkoxy, tri-halomethoxy, N-hydroxysuccinamide, hydroxy, esters, primary amine, secondary amine p-nitrophenol, N-hydroxythalamide, N-hydroxybenzotriazole, chlorine, fluorine, bromine & iodine;

(f) the compound of formula (B) is slurried with methanol and filtered to obtain solid which is washed with methanol and dried to get purified compound formula (B); and (g) treating the compound formula (B) obtained in step (f), with an acid in a suitable solvent to obtain rivaroxaban of formula (I),

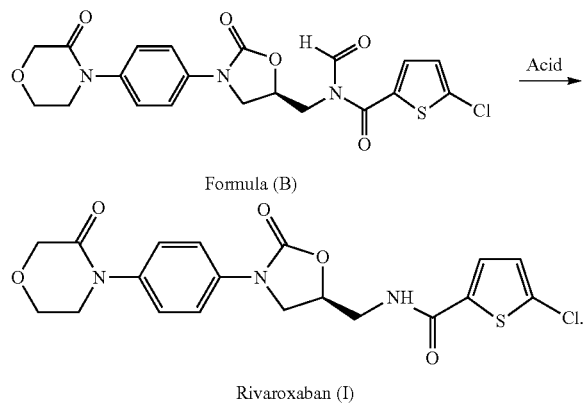

3. The process as claimed in claim 2, wherein in step (b) the solvent used is methylene dichloride and the base used is potassium carbonate.

4. The process as claimed in claim 2, wherein step (c) is carried out in methanol with methylamine as a base to obtain a free base of compound formula (VII).

5. The process as claimed in claim 2, wherein a compound formula (VII) obtained in step (c), is treated with hydrochloric acid to get hydrochloric salt of compound formula (VII).

6. The process as claimed in claim 2, wherein in step (d) the novel intermediate of formula (A) is obtained by treating the compound of formula (VII) with formic acid in suitable solvent(s) selected from methylene dichloride, ethylene dichloride, ether and toluene or mixture thereof.

7. The process as claimed in claim 2, wherein in step (g) the acid used is selected from methane sulphonic acid, hydrochloric acid and sulphuric acid or mixture thereof.

8. The process as claimed in claim 2, wherein in step (g) rivaroxaban is precipitated out by adding methanol as an anti-solvent.

9. The process as claimed in claim 2, wherein step (a) is carried out in suitable solvents independently selected from isopropyl alcohol and water or mixture thereof.

10. The process as claimed in claim 2, wherein in step (d) the novel intermediate of formula (A) is obtained by treating the acid addition salt of compound of formula (VII) with a base to obtain free base of compound of formula (VII), which is further treated with formic acid in suitable solvent (s) selected from methylene dichloride, ethylene dichloride, ether and toluene or mixture thereof.

* * * * *